United States Patent [19]

Lavanish

[11] 4,252,961
[45] Feb. 24, 1981

[54] INTERMEDIATES OF AND PROCESS FOR MAKING 3-[5-[1-(2-, 3-, OR 4-METHYL, OR ETHYL OR ISOPROPYLPHENOXY)ALKYL, ALKYNYL, ALKENYL, OR HALOALKYL]-1,3,4-THIADIAZOL-2-YL]-4-HYDROXY-1-METHYL-2-IMIDAZOLIDI-NONES

[75] Inventor: Jerome M. Lavanish, Akron, Ohio

[73] Assignee: PPG Industries, Inc., Pittsburgh, Pa.

[21] Appl. No.: 123,336

[22] Filed: Feb. 21, 1980

Related U.S. Application Data

[62] Division of Ser. No. 50,025, Jun. 18, 1979.

[51] Int. Cl.$^3$ .............................................. C07D 285/12
[52] U.S. Cl. ...................................... 548/138; 71/90; 548/139; 548/140
[58] Field of Search ......................................... 548/138

[56] References Cited

U.S. PATENT DOCUMENTS

| | | |
|---|---|---|
| 3,758,492 | 9/1973 | Metzger et al. ..................... 548/137 |
| 3,759,939 | 9/1973 | Metzger et al. ..................... 548/137 |
| 3,849,432 | 11/1974 | Metzger et al. ..................... 548/137 |
| 3,901,904 | 8/1975 | Krenzer ............................... 548/137 |
| 3,901,905 | 8/1975 | Krenzer ............................... 548/137 |
| 3,904,640 | 9/1975 | Krenzer ............................... 548/137 |
| 3,920,674 | 11/1975 | Krenzer ............................... 548/137 |
| 3,925,402 | 12/1975 | Krenzer ............................... 548/137 |
| 3,964,895 | 6/1976 | Krenzer ............................... 71/90 |
| 4,012,223 | 3/1977 | Krenzer ............................... 71/90 |
| 4,023,957 | 5/1977 | Krenzer ............................... 71/90 |
| 4,028,375 | 6/1977 | Krenzer ............................... 548/137 |
| 4,036,848 | 7/1977 | Krenzer ............................... 548/137 |
| 4,052,191 | 10/1977 | Krenzer ............................... 71/90 |
| 4,093,443 | 6/1978 | Krenzer ............................... 548/137 |

*Primary Examiner*—Alton D. Rollins
*Attorney, Agent, or Firm*—Edward J. Whitfield; Robert J. Grassi

[57] ABSTRACT

The disclosed compounds such as 3-[5-[1-(2-methylphenoxy)ethyl]-1,3,4-thiadiazol-2-yl]-4-hydroxy-1-methyl-2-imidazolidinone, control weeds preemergence and postemergence.

1 Claim, No Drawings

INTERMEDIATES OF AND PROCESS FOR MAKING 3-[5-[1-(2-, 3-, OR 4-METHYL, OR ETHYL OR ISOPROPYLPHENOXY)ALKYL, ALKYNYL, ALKENYL, OR HALOALKYL]-1,3,4-THIADIAZOL-2-YL]-4-HYDROXY-1-METHYL-2-IMIDAZOLIDINONES

This is a division of application Ser. No. 50,025, filed June 18, 1978.

BACKGROUND OF THE INVENTION

1. Field of the Invention

The invention relates to substituted 1,3,4-thiadiazol-2-yl-4-hydroxy-1-methyl-2-imidazolidinones, particularly to the 3-[5-(1-(2-, 3-, or 4-methyl, -ethyl, or isopropylphenoxyalkyl, alkynyl, alkenyl, or haloalkyl substituted]-1,3,4-thiadiazol-2-yl]-4-hydroxy-1-methyl-2-imidazolidinone compounds.

2. Description of the Prior Art

Imidazolidinones, as a class, are described in patents and chemical literature; none of which, however, teaches or discloses the novel herbicidal compounds described herein and their use to control the weeds described herein.

SUMMARY OF THE INVENTION

The invention described herein concerns novel, agriculturally useful compounds graphically represented by Formula I.

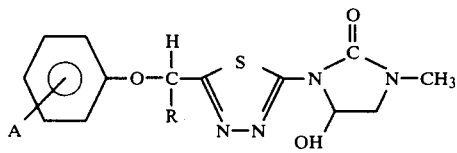

wherein:

A is methyl, ethyl or isopropyl, and R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl; the intermediates graphically represented by Formulas III, IV, and V,

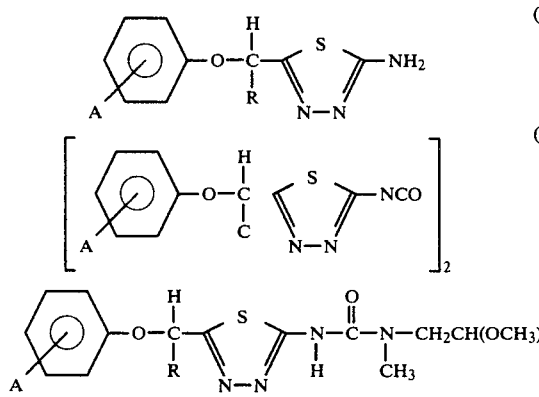

wherein:

A and R are defined as herein, as well as the process for making compounds of the above described formulas. The compounds of Formula I are useful for controlling weeds preemergence and are selective to other weeds both postemergence and preemergence at low application rates of applications. The compounds wherein A is methyl and R is methyl or ethyl, i.e., 3-[5-[1-(2-methylphenoxy)ethyl]-1,3,4-thiadiazol-2-yl]-4-hydroxy-1-methyl-2-imidazolidinone, are useful for controlling morningglory, teaweed, jimsonweed, crabgrass, johnsongrass, coffeeweed, velvetleaf, and barnyardgrass at preemergence rates down to five pounds per acre.

DESCRIPTION OF THE PREFERRED EMBODIMENT

The novel agriculturally useful compounds described herein may be graphically represented by Formula I:

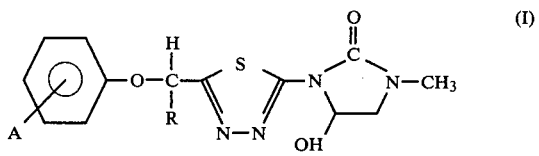

wherein:

A is an alkyl selected from the group consisting of methyl, ethyl, and isopropyl and R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl and 3-bromoethyl.

Examples of compounds represented by Formula I are:

3-[5-[1-(2-methylphenoxy)ethyl]-1,3,4-thiadiazol-2-yl]-4-hydroxy-1-methyl-2-imidazolidinone.

3-[5-[1-(3-ethylphenoxy)-2-bromoethyl]-1,3,4-thiadiazol-2-yl]-4-hydroxy-1-methyl-2-imidazolidinone.

3-[5-[1-(4-isopropylphenoxy)-2-chloroethyl]-1,3,4-thiadiazol-2-yl]-4-hydroxy-1-methyl-2-imidazolidinone.

3-[5-[1-(4-methylphenoxy)-3-chloropropyl]-1,3,4-thiadiazol-2-yl]-4-hydroxy-1-methyl-2-imidazolidinone.

3-[5-[1-(3-ethylphenoxy)-3-bromopropyl]-1,3,4-thiadiazol-2-yl-4-hydroxy-1-methyl-2-imidazolidinone.

3-[5-[1-(2-isopropylphenoxy)-2-propynyl]-1,3,4-thiadiazol-2-yl]-4-hydroxy-1-methyl-2-imidazolidinone.

3-[5-[1-(3-methylphenoxy)-2-butynyl]-1,3,4-thiadiazol-2-yl]-4-hydroxy-1-methyl-2-imidazolidinone.

3-[5-[1-(4-ethylphenoxy)-3-butynyl]-1,3,4-thiadiazol-2-ylp-4-hydroxy-1-methyl-2-imidazolidinone.

3-[5-[1-(3-isopropylphenoxy)-2-propenyl]-1,3,4-thiadiazol-2-yl]-4-hydroxy-1-methyl-2-imidazolidinone.

3-[5-[-1-(4-methylphenoxy)-2-butenyl]-1,3,4-thiadiazol-2-yl]-4-hydroxy-1-methyl-2-imidazolidinone.

3-[5-[1-(3-ethylphenoxy)-2-chloroethyl]-1,3,4-thiadiazol-2-yl]-4-hydroxy-1-methyl-2-imidazolidinone.

3-[5-[1-(2-isopropylphenoxy)-2-bromomethyl]-1,3,4-thiadiazol-2yl]-4-hydroxy-1-methyl-2-imidazolidinone.

3-[5-[1-(4-ethylphenoxy)-3-chloropropyl]-1,3,4-thfadiazol-2-yl]-4-hydroxy-1-methyl-2-imidazolidinone.

3-[5-[1-(4-methylphenoxy)-3-bromopropyl]-1,3,4-thfadiazol-2-yl]-4-hydroxy-1-methyl-2-imidazolidinone.

3-[5-[1-(2-isopropylphenoxy)-3-butenyl]-1,3,4-thiadiazol-2-yl]-4-hydroxy-1-methyl-2-imidazolidinone.

3-[5-[1-(3-methylphenoxy)-2-pentenyl]-1,3,4-thiadiazol-2-yl]-4-hydroxy-1-methyl-2-imidazolidinone.

3-[5-[1-(4-ethylphenoxy)-1-(3-methylbutyl)]-1,3,4-thiadiazol-2yl]-4-hydroxy-1-methyl-2-imidazolidinone.

3-[5-[1-(4-isopropylphenoxy)-2-(2-methylbutyl)]-1,3,4-thiadiazol-2-yl]-4-hydroxy-1-methyl-2-imidazolidinone.

3-[5-[1(2-methylphenoxy)-1(2,2-dimethylpropyl)]-1,3,4-thiadiazol-2-yl]-4-hydroxy-1-methyl-2-imidazolidinone.

3-[5-[1-(3-ethylphenoxy)-1-butyl]-1,3,4-thiadiazol-2-yl]-4-hydroxy-1-methyl-2-imidazolidinone.

3-[5-[1-(4-isopropylphenoxy)-2-(2-methylpropyl)]-1,3,4-thiadiazol-2-yl]-4-hydroxy-1-methyl-2-imidazolidinone.

3-[5-[1-(3-methylphenoxy)propyl]-1,3,4-thiadiazol-2-yl]-4-hydroxy-1-methyl-2-imidazolidinone.

Although all of the compounds described herein are useful for the purpose described herein, some compounds are more useful than others. Compounds in which R is an alkynyl, are of a general utility, while those compounds in which R is an alkenyl, are of better utility. Compounds in which R is a haloalkyl described herein are of high utility and of these, the preferred compounds are those in which R is chloromethyl or bromoethyl. Compounds in which R is an alkyl described herein, are greatly preferred and highly preferred are compounds in which the alkyl is methyl or ethyl or propyl. Compounds in which A is methyl are the especially preferred. The following compounds are the most preferred: 3-[5-(1-(2-methylphenoxypropyl)-1,3,4-thiadiazol-2-yl]-4-hydroxy-1-methyl-2-imidazolidinone, 3-[5-(1-(2-methylphenoxy)ethyl)-1,3,4-thiadiazol-2-yl]-4-hydroxy-1-methyl-2-imidazolidinone, and 3-[5-(1-(4-methylphenoxyethyl)-1,3,4-thiadiazol-2-yl]-4-hydroxy-1-methyl-2-imidazolidinone.

SYNTHESIS OF THE COMPOUNDS

The synthesis of the compounds proceeds according to the general reactions 1, 2, 3 and 4 shown below:

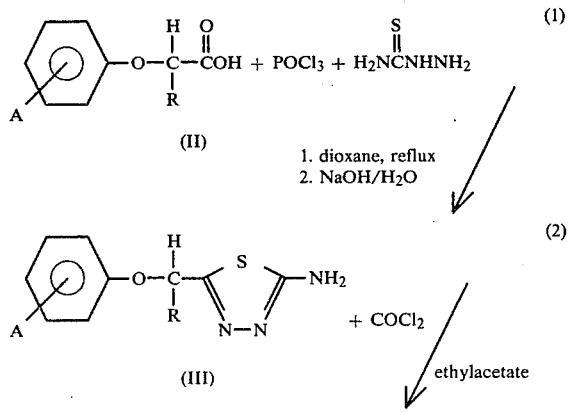

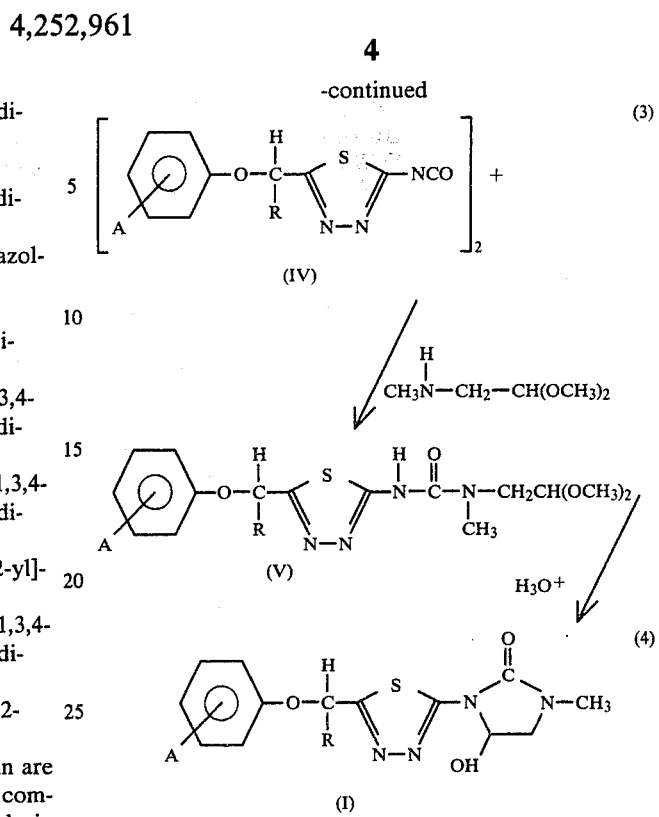

PREPARATION OF 5-SUBSTITUTED 2-AMINO-1,3,4-THIADIAZOLE

The proper alpha substituted carboxylic acid graphically represented by Formula II, wherein R is as described herein (typically 0.4–0.5 moles), an equimolar amount of thiosemicarbazide, and 30 milliliters of dry dioxane are charged into a hundred milliliter reactor equipped with a thermometer, an efficient stirrer, pressure equalized addition funnel and a condenser-drying tube. The addition funnel is charged with approximately 10 percent excess of phosphorus oxychloride which is added drop-wise so as to maintain a reaction temperature of 85°–90° C. and reaction occurs as shown by reaction equation 1. The mixture is then heated to reflux for about 1 hour, after which the solvent is flashed off using a vacuum such as a water aspirator. Water (50 milliliters) is added to the residue to give an emulsion which is then made basic with a 50 percent hydroxide solution. In those instances that a solid product is obtained (graphically represented by Formula III, wherein R is as described herein) the product is isolated by filtration, and recrystallized when necessary. In other cases, the reaction mixture is extracted with ether, the ether layer is separated from the heavier layers, dried over magnesium sulfate, filtered and concentrated under vacuum to give the crude product represented as a viscous oil.

PREPARATION OF THE ISOCYANATE DIMERS

Five to 10 grams of the appropriate 2-amino-1,3,4-thiadiazol (graphically represented by Formula III) is added to a solution of phosgene in ethylacetate, (or other suitable solvent) prepared by saturating 50–100 milliliters of solvent with phosgene at room temperature when adding another 50–100 milliliters of solvent (see reaction equation 2). The mixture is allowed to stir overnight at room temperature and then purged with nitrogen or argon to remove the unreacted phosgene. In those cases where a solid was obtained the product (graphically represented by Formula IV), which is an isocyanate dimer of the appropriate substituted 1,3,4-thiadiazole, was isolated by filtration and dried. In cases where no solid product is evident, the reaction mixture may be topped under vacuum to give the product as a viscous oil or glass.

PREPARATION OF ACETAL UREAS

The appropriate isocyanate dimer of Formula IV and an equivalent amount of methylaminoacetaldehyde dimethylacetal were heated to reflux (5–15 minutes) in an inert solvent such as ether, benzene or toluene, and the reaction proceeded as shown by reaction equation 3 so as to form the product graphically represented by Formula V. Some products may be produced as crystals directly from solution, and others may be induced to crystallize by addition of hexane. The product represented by graphic Formula V may be purified such as by washing with ether or hexane or recrystallized from hexane/benzene or from ether/benzene or from ether/chloroform/benzene solutions. Those products or compounds that are represented by Formula V obtained as oils need not be purified.

PREPARATION OF THE COMPOUNDS OF FORMULA I

The appropriate acetal urea of Formula V (approximately three to four grams) is added to 150–200 milliliters of water containing 1.5–2 milliliters of concentrated hydrochloric acid. The mixture is stirred vigorously and heated to reflux, and reaction proceeds as shown by reaction equation 4. The hydrolysis is monitored by thin layer chromatography (alumina-ethylacetate) until complete, and the product containing a compound of Formula I forms. The product, in some cases, may be crystallized directly from the reaction mixture upon cooling. In other cases, the compounds of Formula I are extracted with chloroform and isolated by stirring the solvent under vacuum. Those compounds which solidify upon concentration are further purified. In some cases, the compounds may be used directly as obtained. In other cases, crystallization is induced by seeding an ether solution with a related compound, which may then be further purified.

EXAMPLE

The following example illustrates the synthesis of the compounds described herein.

Example I
3-[5-[1-(2-methylphenoxy)ethyl]-1,3,4-thiadiazol-2-yl]-4-hydroxy-1-methyl-2-imidazolidinone a. Formation of 5-[1-(2-methylphenoxy)ethyl]-2-amino-1,3,4-thiadiazole

A 100 milliliter flask adapted with a paddle stirrer, thermometer, an addition funnel, condenser and drying tube was charged with 7.2 grams (0.040 mole) of 2-(2-methylphenoxy)propanoic acid, 3.6 grams, (0.040 mole) of thiosemicarbazide and 30 milliliters of dioxane. The slurry was heated to 90° C. and the addition funnel was charged with phosphorous oxychloride ($POCl_3$). The $POCl_3$ (6.7 grams; 0.044 mole) was slowly added (for 20 minutes) while maintaining the temperature within 90°–95° C., a gooey white precipitate formed. When the addition was completed the mixture was refluxed for 60 minutes. The flask was evacuated by using a water aspirator to remove volatiles (HCl, $POCl_3$ and some dioxane), and then 50 milliliters of water was added and mixture was made basic by the addition of 50 percent solution of NaOH until the pH of the solution was 10. The white precipitate was filtered off, washed with water and dissolved in the minimum amount of 95 percent ethanol, to which a small amount of a 10 percent sodium hydroxide solution was added to make the ethanol solution basic. Water was added until a precipitate formed and the solution was cooled in the refrigerator, then suctioned filtered. The precipitate was washed with water, and dried in a vacuum oven at 70° C. to white crystals of 5-[1-(2-methylphenoxy)ethyl]-2-amino-1,3,4-thiadiazole (6.8 grams—melting point 176°–179° C.)

b. Formation of 5-[1-(2-methylphenoxy)ethyl]-1,3,4-thiadiazol-2-yl isocyanate dimer A 500 milliliter, 3-neck flask equipped with a magnetic stirrer, thermometer, dry ice condenser/drying tube and inlet from a phosgene ($COCl_2$) tank via a calibrated rotometer was charged with 50 milliliters of ethylacetate which was saturated with phosgene at 20° C. (approximately 0.5 mole of phosgene) and cooled in an ice bath. An additional 50 milliliters of ethylacetate was added and then 6.8 grams of 5-[1-(2-methylphenoxy)ethyl]-2-amino-1,3,4-thiadiazole, (prepared above); a cloudy solution formed, the solution was stirred overnight, and then filtered to remove a small amount of insoluble sediment. The clear solution was topped on a roto-vac at 70° C. to form 8.1 grams of a viscous yellow residue of 5-[1-(2-methylphenoxy)ethyl]-1,3,4-thiadiazol-2-yl isocyanate dimer.

c. Formation of 3-[5-[1-(2-methylphenoxy)ethyl]-1,3,4-thiadiazol-2-yl]-1-methyl-1-(2,2-dimethoxyethyl)urea Methylaminoacetaldehyde dimethylacetal (3.7 grams, 0.031 mole) was added to a 40 milliliter benzene solution containing 8.1 grams (0.031 equivalent) of the 5-(1-(2-methylphenoxy)ethyl)-1,3,4-thiadiazol-2-yl isocyanate dimer (prepared above) and the resulting solution was refluxed for 15 minutes and then cooled. Hexane (150 milliliters) was added and the resulting coludy solution gave a small amount of fluffy crystals and was allowed to stand but no further crystallization occurred. The solution was filtered, topped on a roto-vac at 70° C. to form a pale yellow oily viscous liquid, which was left to stand overnight. No crystals formed and the liquid (10.3 grams) was shown by thin layer chromatography to be nearly pure 3-[5-[1-(2-methylphenoxy)ethyl]-1,3,4-thiadiazol-2-yl]-1-methyl-1-(2,2-dimethoxyethyl)urea.

d. Synthesis of 3-[5-[1-(2-methylphenoxy)ethyl]-1,3,4-thiadiazol-2-yl]-1-methyl-4-hydroxy-2-imidazolidinone A mixture containing 4.0 grams of the 3-[5-[1-(2-methylphenoxy)ethyl]-1,3,4-thiadiazol-1-yl]-1-methyl-(2,2-dimethoxyethyl)urea (prepared above), 150 milliliters of water and 1.5 milliliters of concentrated hydrochloric acid (HCl) was refluxed for 35 minutes, then cooled overnight. The reaction mixture was extracted with chloroform, and the organic phase was dried over magnesium sulfate ($MgSO_4$), filtered and topped on a roto-vac at 70° C. to yield 3.3 grams of a pale yellow goo. It was dissolved in ethyl acetate and chromatographed on activity I alumina with ethyl acetate followed by methanol. The fractions containing the least mobile TLC spot were collected, and the solvent evaporated off on a roto-vac at 70° C. to yield 2.1 grams of a viscous pale yellow oil of 3-[5-[1-(2-methylphenoxy)ethyl]-1,3,4-thiadiazol-2-yl]-1-methyl-4-hydroxy-2-imidazolidinone.

Example II

3-[5-[1-(3-methylphenoxy]ethyl)-1,3,4-thiadiazol-2-yl]-4-hydroxy-1-methyl-2-imidazolidinone a. Formation of 5-[1-(3-methyl)phenoxy)ethyl]-2-amino-1,3,4-thiadiazole

The procedure of Example I a. was followed using 2-(3-methylphenoxy)propanoic acid. The white crystals formed were recrystallized from the minimum amount of ethanol-water mixture, filtered off, washed with water and dried in a vacuum oven at 80° C. to 7.1 grams of white crystals of 5-[1-(3-methylphenoxy)ethyl]-2-amino-1,3,4-thiadiazole, (melting point 154°–157° C.).

b. Formation of 5-[1-(3-methylphenoxy)ethyl]-1,3,4-thiadiazol-2-yl isocyanate dimer The procedure of Example I b. was followed using 7.1 grams of the above prepared 5-[-1-(3-methylphenoxy)]ethyl-2-amino-1,3,4-thiadiazole to form 8.0 grams of a pale viscous oil of 5-[1-(3-methylphenoxy)ethyl]-1,3,4-thiadiazol-2-yl isocyanate dimer.

c. Formation of 3-[5-[1-(3-methylphenoxy)ethyl]-1,3,4-thiadiazol-2-yl]-1-methyl-1-(2,2-dimethoxyethyl)urea Methylaminoacetaldehyde dimethylacetal (3.7 grams, 0.031 mole) was added to a 50 milliliter benzene solution containing 3.7 grams (0.031 equivalent) of the 5-[1-(3-methylphenoxy)ethyl]-1,3,4-thiadiazol-2-yl isocyanate dimer (prepared above) and the resulting solution was refluxed for 15 minutes and then cooled. Hexane (100 milliliters) was added and the resulting solution formed crystals which were filtered off, and dried in a vacuum oven at 80° C. to 9.0 grams of white crystals of [5-[1-(3-methylphenoxy)ethyl]-1,3,4thiadiazol-2-yl]-1-methyl-1-(2,2-dimethoxyethyl)urea (melting point 122°–125° C.).

d. Synethsis of 3-[5-[1-(3-methylphenoxy)ethyl]-1,3,4-thiadiazol-2-yl]-1-methyl-4-hydroxy-2-imidazolidinone A mixture containing 4.0 grams of the 3-[5-[1-(3-methylphenoxy)ethyl]-1,3,4-thiadiazol-2-yl]-1-methyl-1-(2,2-dimethoxyethyl)urea (prepared above, 200 milliliters of water and 2.0 milliliters of concentrated hydrochloric acid (HCl) was refluxed for 20 minutes, and then cooled. An oil formed which was extracted with chloroform, and the chloroform extract was dried over magnesium sulfate (MgSO4), filtered and topped on a roto-vac at 70° C. to yield 4.1 grams of a viscous oil which was mixed with diethylether and crystals formed. The crystals were filtered off, dried in a vacuum oven at 80° C. to white crystals of 3-[5-[1-(3-methylphenoxy)ethyl]-1,3,4-thiadiazol-2-yl]-1-methyl-4-hydroxy-2-imidazolidinone (melting point 130°–133° C.).

Example III

3-[5-[1-(4-methylphenoxy)ethyl]-1,3,4-thiadiazol-2-yl]-4-hydroxy-1-methyl-2-imidazolidinone a. Formation of 5-[1-(4-methylphenoxy)ethyl]-2-amino-1,3,4-thiadiazole

A 100 milliliter flask adapted with a paddle stirrer, thermometer, addition funnel, condenser and drying tube was charged with 7.2 grams (0.040 mole) of 2-(4-methylphenoxy)propanoic acid, 3.6 grams (0.040 mole) of thiosemicarbazide and 30 milliliters of dioxane, and heated to 90° C. the addition funnel was charged with phosphorous oxychloride (POCl3), (6.7 grams, 0.4 mole) which was slowly added for 15 minutes while maintaining the temperature within 90°–95° C. When the addition was completed, the mixture was refluxed for 60 minutes. The flask was evacuated by using a water aspirator to remove volatiles (HCl, POCl3 and some dioxane), and then 50 milliliters of water was added and mixture was made basic by the addition of 50 percent solution of NaOH until the pH of the solution was 10. The white precipitate was filtered off, washed with water and dried in a vacuum oven at 80° C. to 7.7 grams of tan crystals (melting point 142°–162° C.) which were recrystallized from the minimum amount of a water ethanol mixture, filtered off and dried in a vacuum oven at 80° C. to 4.8 grams of yellow crystals of 5-[1-(4-methylphenoxy)ethyl]-2-amino-1,3,4-thiadiazole (melting point 178°–180° C.).

b. Formation of 5-[1-(4-methylphenoxy)ethyl]-1,3,4-thiadiazol-2-yl isocyanate dimer A 500 milliliter, 3-neck flask equipped with a magnetic stirrer, thermometer, dry ice condenser/drying tube and inlet from a phosgene (COCl2) tank via a calibrated rotometer was charged with 50 milliliters of ethylacetate which was saturated with phosgene at 20° C. (approximately 0.5 mole of phosgene) and cooled in an ice bath. An additional 50 milliliters of ethylacetate was added and then 4.8 grams of 5-[1-(4-methylphenoxy)ethyl]-2-amino-1,3,4-thiadiazole (prepared above) was added, the solution was stirred overnight and then filtered to remove a small amount of insoluble sediment. The clear solution was topped on a roto-vac at 70° C. to form 4.0 grams of a viscous orange oil of 5-[1-(4-methylphenoxy)ethyl]-1,3,4-thiadiazol-2-yl isocyanate dimer.

c. Formation of 3-[5-[1-(4-methylphenoxy)ethyl]-1,3,4-thidiazol-2-yl]-1-methyl-1-(2,2-dimethoxyethyl)urea Methylaminoacetaldehyde dimethylacetal (1.8 grams, 0.015 mole) was added to a benzene solution containing 4.0 grams (0.015 mole) of the 5-[1-(4-methylphenoxy)ethyl]-1,3,4-thiadiazol-2-yl isocyanate dimer (prepared above). The resulting solution was refluxed for 20 minutes, topped on a roto-vac at 70° C. to form a viscous red-orange oil, which was redissolved in benzene-hexane mixture and left to stand overnight. Crystals formed which were removed by suction filtration, and dried in a vacuum oven at 70° C. to 3.2 grams of tan crystals of [5-[1-(4-methylphenoxy)ethyl]-1,3,4-thiadiazol-2-yl-1-methyl-1-(2,2-dimethoxyethyl)urea, (melting point 94°–100° C.).

d. Synthesis of 3-[5-[1-(4-methoxyphenoxy)ethyl]-1,3,4-thiadiazol-2-yl]-1-methyl-4-hydroxy-2-imidazolidinone A mixture containing 3.5 grams of the 3-[5-[1-(4-methylphenoxy)ethyl]-1,3,4-thiadiazol-2-yl]-1-methyl-2,2-dimethoxyethyl)urea (prepared above), 150 milliliters of water and 1.5 milliliters of concentrated hydrochloric acid (HCl) was refluxed for 25 minutes, then cooled with formation of an oil. The oil was extracted with chloroform, and the chloroform extract was dried over magnesium sulfate (MgSO$_4$), filtered and topped on a roto-vac at 70° C. to yield 3.2 grams of an orange oil. It was dissolved in diethylether and heated with formation of crystals which were filtered off and dried in a vacuum oven at 70° C. to 1.8 grams of ivory crystals of [5-[1-(4-methylphenoxy)ethyl-1,3,4-thiadiazol-2-yl]-1-methyl-4-hydroxy-2-imidazolidinone, (melting point 126°-128° C.).

INTERMEDIATE COMPOUNDS

The other compounds described herein and represented graphically by Formulas III and IV, do not possess herbicidal properties and the compounds represented by Formula V show herbicidal properties, but all the compounds represented by Formula III, IV and V are very useful intermediates in the synthesis of the novel useful compounds represented by Formula I.

APPLICATIONS OF THE COMPOSITIONS AGAINST WEEDS

The novel active compounds of Formula I are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area and the like. Thus while the application of up to only about one or two ounces of active compound per acre may be sufficient for good control of a light infestation of weeds growing under adverse conditions, the application of 2 pounds or 10 pounds or more of an active compound of Formula I per acre may be required for good control of a dense infestation of hardy perennial weeds growing under favorable conditions.

a. Examples Of Weeds Which May Be Controlled By The Compounds Described Herein Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. The compositions set forth herein, when applied in a herbicidally effective amount control field pennycress, ryegrass, goosegrass, chickweed, purslane, smartweed, knotweed, wildbuckwheat, kochia, medic, corn cockle, ragweed, sow-thistle, croton, cuphea, dodder, fumitory, groundsel, hempnettle, knawel, spurge, sprurry emex, jungle rice, pondweed, dogfennel, carpetweed, bedstraw, ducksalad, naiad, chestgrass, fall panicum, witchgrass, switchgrass, watergrass, teaseed, wild turnip and sprangletop; biennials such as wild carrot, matricaria, wild barley, campion, chamomile, burdock, mullein, roundleaved mallow, bull thistle, houndstongue, moth mullein and purple star thistle; or perennials such as white cockle, perennial ryegrass, quackgrass, canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cat-tail, wintercress, horsenettle, nutsedge, milkweed and sicklepod.

However, important noxious weeds of the genera against which the compounds of the invention are most effective preemergence at ten pounds per acre are: Sida, Datura, Brassica, Setaria, Digitaria, Sorghum, Sesbania, Abutilon, Ipomoea, Avena and Echinochola. Weed species against which the compounds of the invention are most effective preemergence are: *Sida spinosa* (L) (teaweed), *Datura stramonium* (L) (jimsonweed), *Brassica kaber* (L) (wild mustard), *Sorghum halepense* (L) (johnsongrass), *Digitaria sanguinalis* (L) (crabgrass), *Setaria glauca* (L) (yellow foxtail), *Sesbania spp.* (coffeeweed), *Abutilon theophrasti* (L) (velvetleaf), *Ipomoea purpurea* (L) Roth (tall morningglory) and *Echinochola crusgalli* (L) (barnyardgrass). When applied at very low rates, up to 5 pounds per acre, the weed species most affected preemergence by the preferred compounds where A is methyl and R is methyl or ethyl are: *Sida spinosa* (1) (teaweed), *Datura stramonium* (L) (jimsonweed), *Digitaria sanguinalis* (L) (crabgrass), *Sorghum halepense* (L) (johnsongrass), *Abutilon theophrasti* (L) velvetleaf) and *Echinochola crusgalli* (L) (barnyardgrass).

Weeds against which the compositions are most effective when applied postemergence at ten pounds per acre are the genera Ipomoea, Brassica, Sesbania, Abutilon and Echinochola and the species *Ipomoea purpurea* (L) Roth (tall morningglory), *Brassica kaber* (L) (wild mustard), *Sesbania spp.* (coffeeweed), *Abutilon theophrasti (L) (velvetleaf) and Echinochola crusgalli* (L) (barnyardgrass). Compositions in which A is methyl and located at the 3 (meta) or 4 (para) position or R is methyl are effective postemergence against broadleaf and grassy weeds.

b. Description Of The Method Of Controlling Weeds

As used herein and in the claims, the method of controlling the weeds comprises contacting the weeds with a herbicidally effective amount of a composition represented by the general formula described herein. The term "contacting the weeds" refers to any method of contacting the weeds, both preemergence (before the weeds appear) and/or postemergence (after the weeds appear), such as applying granules of the compounds to the soil prior to emergence or spraying a solution of the compound or compounds described by the general formula, or any other method known in the art by which the weeds are contacted either before they emerge or after they emerge, or both before and after they emerge, with one or more of the compounds represented by Formula I described herein. The most preferred method is by contacting the weeds preemergence, especially at slow rates such as 5 pounds per acre. The phrase "herbicidally effective amount" refers to that amount required under the environmental conditions in order to effectively control, that is, by which the weeds are injured so as not to be able to recover from the application of the compound, or to be killed by the compound.

c. General Application Of The Compounds

For practical use of herbicides the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculties, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsfier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestations.

A typical herbicidal formulation according to this invention is illustrated by the following example, in which the quantities are in parts by weight.

Example IV

| Preparation of a Dust | |
|---|---|
| Product of Example I | 10 |
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Mixtures Of Compounds Alone Or In Mixtures

Although all of the compounds described herein and represented by the general formula described herein are useful as herbicides, some of these are preferred and are better for applications against weeds. In general, all of the compounds described herein may be used either alone or together in mixtures. When use in mixtures the amount or ratio of one compound to another may vary from 0.01 to 100.

e. Manner Of Application Of The Compounds Of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations will comprise from about 0.05 to about 95 percent by weight of the active compounds of this invention. In a preferred embodiment of this invention, the herbicidal formulations can also comprise other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, desiccants, growth inhibitors and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples Of Other Pesticides And Herbicides For Combinations

The other herbicides, defoliants, desiccants and plant growth inhibitors, with which the compounds of this invention can be used in the herbicidal formulations to control weeds can include: chlorophenoxy herbicides such as: 2,4-D, 2,4,5-T, MCPA, MCPB, 4-(2,4-DB), 2,4-DEB, 4-CPB 4-CPA, 5-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as: CDEC, metam sodium, EPTC, diallate, PEBC, perbulate, vernolate and the like; substituted urea herbicides such as: norea, siduron, dichloroal urea, chloroxuron cycluron, fenuron, monuron, monuron TCA, diuron, linuron, monolinuron, neburon, buturon, trimeturon, trimeturon and the like; symmetrical triazine herbicides such as: simazine, chlorazine, atraone, desmetryne, norazine, ipazine, prometryn, atrazine, trietazine, simetone, prometone, propazine, ametryne and the like; chloroacetamide herbicides such as: alpha-chloro-N,N-dimethylacetamide, CDEA, CDAA, alphachloro-N-isopropyl-acetamide, 2-chloro-N-isopropylacetanilide, 4-(chloroacetyl) morpholine, 1-(chloroacetyl) piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenyl-acetic acid, 2-methoxy-3,5,6-trichlorophenylacetic acid, 2,5-dichloro-3-nitrobenzoic acid, dual, metribuzin and the like; and such compounds as aminotriazole, maleic hydrazode, phenyl mercuric acetate, endothall biuret, technical chlordane, dimethyl 2,3,5,6-tetrchlorotetephthalate, diquat, erbon, DNC, DNBP, dichlorobenil, CPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dine, bromoxynil, cacodylic acid, CMA, CPMF, cypromid, DCB, DCPA, dichlone, diphenatril, DMTT, DMAP, EXD, ioxynil, isocil, potassium cyanate, MAA, MAMA, MCPES, MCPP, MH, molinate, NPA, paraquat, PCP, picloram, DPA, PCA, phrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides and other derivatives whenever applicable to the particular parent compounds.

g. Examples of Herbicidal Control

The following examples illustrate the method of controlling the weeds described herein. These examples were conducted under standard laboratory conditions, using standard laboratory procedures.

Example V

When the compound of 3-[5-[1-(2-methylphenoxy)ethyl]-1,3,4-thiadiazol-2-yl]-4-hydroxy-1-methyl-2-imidazolidinone (Example I) was applied preemergence at ten pounds per acre to the weed species: *Sida spinosa* (L) (teaweed), Sesbania (coffeeweed), *Datura stramonium* (L) (jimsonweed), *Brassica kaber* (L) (wild mustard), *Sorghum halepense* (L) (johnsongrass), *Ipomoea purpurea* (L) Roth (tall morningglory), *Echinochola crusgalli* (L) (barnyardgrass), *Digitaria sanguinalis* (L) (crabgrass) and *Setaria glauca* (yellow foxtail), at the end of twenty-one (21) days all of the weed species were killed.

Example VI

When the compound of 3-[5-[1-(3-methylphenoxy)ethyl]-1,3,4-thiadiazol-2-yl]-4-hydroxy-1-methyl-2-imidazolidinone (Example II) was applied preemergence under the same conditions at 10 pounds per acre to the weed species as in Example V, at the end of twenty-one (21) days all of the weed species were killed.

Example VII

When the compound of 3-[5-[1-(4-methylphenoxy)ethyl]-1,3,4-thiadiazol-2-yl]-4-hydroxy-1-methyl-2-imidazolidinone (Example III) was applied preemergence under the same conditions at 10 pounds per acre to the weed species as in Example V, at the end of twenty-one (21) days all of the weed species were killed.

Example VIII

When the compound 3-(5-phenoxymethyl-1,3,4-thiadiazol-2-yl)-4-hydroxy-1-methyl-2-imidazolidinone, which was prepared in a manner similar to that of the compound of Example I was applied to the same weed species under the same conditions as in Example V, all of the weed species were growing.

The compounds of Formula I are safe to crops, for example, corn and wheat, so that prememergence applications may be made while crops are planted or are growing before the weeds emerge.

While the invention has been described with reference to the specific details of certain illustrative embodiments, it is not intended that it shall be limited thereby except so far as such details appear in the accompanying claims.

I claim:

1. A compound graphically represented by Formula III:

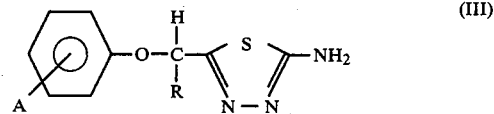

wherein:
A is an alkyl selected from the group consisting of methyl, ethyl and isopropyl, and,
R is an alkyl of up to four carbon atoms, an alkenyl of up to three carbon atoms, an alkynyl of up to three carbon atoms or a haloalkyl selected from the group consisting of chloromethyl, bromomethyl, 2-chloroethyl and 2-bromomethyl.

* * * * *

UNITED STATES PATENT AND TRADEMARK OFFICE
CERTIFICATE OF CORRECTION

PATENT NO. : 4,252,961

DATED : February 24, 1981

INVENTOR(S) : Jerome M. Lavanish

It is certified that error appears in the above-identified patent and that said Letters Patent are hereby corrected as shown below:

In Claim 1, column 14, line 46, "2-bromomethyl" should read --2-bromoethyl--.

Signed and Sealed this

Twenty-fifth Day of August 1981

[SEAL]

Attest:

Attesting Officer

GERALD J. MOSSINGHOFF

Commissioner of Patents and Trademarks